United States Patent
Hovland et al.

(10) Patent No.: US 8,449,487 B2
(45) Date of Patent: May 28, 2013

(54) BLOOD TREATMENT APPARATUS

(75) Inventors: Roy Hovland, Denver, CO (US);
Anders Wallenborg, Bjärred (SE)

(73) Assignee: Gambro Lundia AB, Lund (SE)

( * ) Notice: Subject to any disclaimer, the term of this patent is extended or adjusted under 35 U.S.C. 154(b) by 785 days.

(21) Appl. No.: 12/516,786

(22) PCT Filed: Dec. 1, 2006

(86) PCT No.: PCT/IB2006/003434
§ 371 (c)(1),
(2), (4) Date: Dec. 21, 2009

(87) PCT Pub. No.: WO2008/065470
PCT Pub. Date: Jun. 5, 2008

(65) Prior Publication Data
US 2010/0106071 A1    Apr. 29, 2010

(51) Int. Cl.
*A61M 1/16* (2006.01)

(52) U.S. Cl.
USPC .......................... 604/5.01; 604/4.01; 604/5.04

(58) Field of Classification Search
USPC ................... 210/87, 134, 646, 739; 604/5.01, 604/6.1, 6.11, 4.01, 5.02, 5.03, 5.04, 6.01
See application file for complete search history.

(56) References Cited

U.S. PATENT DOCUMENTS

| | | | |
|---|---|---|---|
| 3,528,550 A | 9/1970 | Cappelen, Jr. | |
| 3,738,382 A | 6/1973 | Cappelen, Jr. et al. | |
| 3,878,095 A * | 4/1975 | Frasier et al. | 210/87 |
| 4,153,554 A | 5/1979 | von der Heide et al. | |
| 4,229,299 A | 10/1980 | Savitz et al. | |
| 4,298,357 A * | 11/1981 | Pernic | 96/174 |
| 4,348,280 A | 9/1982 | George et al. | |
| 4,828,693 A | 5/1989 | Lindsay et al. | |
| 4,997,570 A * | 3/1991 | Polaschegg | 210/646 |
| 5,624,551 A * | 4/1997 | Baumann et al. | 210/134 |
| 5,674,390 A * | 10/1997 | Matthews et al. | 210/261 |
| 5,762,782 A | 6/1998 | Kenley et al. | |

(Continued)

FOREIGN PATENT DOCUMENTS

| | | |
|---|---|---|
| EP | 0 161 686 A2 | 11/1985 |
| FR | 2126610 A | 10/1972 |
| WO | 00/57935 A1 | 10/2000 |

OTHER PUBLICATIONS

Gambro Lundia AB, AK 200 Maintenance Manual, p. 2:26 (2001).

(Continued)

*Primary Examiner* — Tatyana Zalukaeva
*Assistant Examiner* — Benjamin Klein
(74) *Attorney, Agent, or Firm* — Pearne & Gordon LLP

(57) ABSTRACT

A blood treatment apparatus (1) comprising a degassing unit (15) receiving gas-containing fluid and supplying degassed fluid to a fluid chamber (3) of a blood treatment unit (2). The degassing unit has a gas separator (16), a degassing pump (18) to circulate fluid in a degassing line (12), a flow restrictor (17) for reducing the pressure in the degassing line (12), an absolute pressure sensor (19), and a control unit (20) designed to control the speed of said degassing pump from the absolute pressure signal emitted by the pressure sensor. The apparatus comprises a dialysis machine provided with a device for preparing on-line a dialysis liquid from water and concentrates. The apparatus achieves an accurate and reliable regulation of a desired concentration of gas in the dialysis liquid.

26 Claims, 2 Drawing Sheets

U.S. PATENT DOCUMENTS

| | | | |
|---|---|---|---|
| 7,473,395 B2 * | 1/2009 | Zviman et al. | 422/46 |
| 2004/0057037 A1 | 3/2004 | Ohishi et al. | |
| 2005/0242034 A1 * | 11/2005 | Connell et al. | 210/646 |
| 2007/0179433 A1 * | 8/2007 | Jonsson et al. | 604/31 |
| 2007/0278155 A1 * | 12/2007 | Lo et al. | 210/646 |
| 2009/0151470 A1 * | 6/2009 | Puppini et al. | 73/861 |
| 2010/0268145 A1 * | 10/2010 | Caleffi et al. | 604/5.04 |

OTHER PUBLICATIONS

Gambro Lundia AB, AK 200 Replacements, p. 3:3 (1999).

Gambro Lundia AB, Service Technicians Guide, pp. 4:13 and 4:19 (1999).

Gambro Lundia AB, Technical Description Fluid Monitor, pp. 5:5, 5:7, and 5:12 (1999).

Gambro Lundia AB, BiCart Select System, pp. 10:5 and 10:6 (1999).

Gambro Lundia AB, Technical Description, pp. 2:4, 2:5, 2:11, and 2:12 (2005).

Gambro Lundia AB, Calibrations, p. 6:11 (2005).

Gambro Lundia AB, AK 100 Maintenance Manual, p. 29 (1998).

Gambro Lundia AB, Service Technicians Guide, pp. 5:9 and 5:15 (1995).

Gambro Lundia AB, Technical Description Fluid Monitor, pp. 6:5 and 6:12 (1995).

\* cited by examiner

BLOOD TREATMENT APPARATUS

BACKGROUND OF THE INVENTION

The invention relates to a blood treatment apparatus, and particularly to a blood treatment apparatus provided with a device for on-line preparation of a treatment liquid.

Specifically, though not exclusively the invention can be usefully applied in a dialysis machine provided with a device for preparing on-line a dialysis liquid from water and concentrates.

As is well known, air bubbles in the dialysis liquid render inoperative the semipermeable membrane of the dialyzer. Therefore a dialysis machine normally includes a device for removing gas and minimizing gas in the dialysis liquid. For example, one type of gas removal system, as shown in U.S. Pat. No. 3,738,382, includes a heater for heating the water to a high temperature and a debubbling chamber for removing gas from the heated water at atmospheric pressure. This system does not effectively degass the water and the heating of the water causes dissolved minerals to precipitate and clog passageways within the dialysis machine. A second type of gas removal system is shown in U.S. Pat. No. 3,528,550. In this system water is fed to a degassing chamber which is maintained at a pressure below atmospheric pressure by a Venturi through which dialysis solution flows. Thus the pressure in the degassing chamber is directly related to the dialysis solution flow rate through the Venturi. The Venturi only applies a moderately negative pressure to the degassing tank and thus does not effectively degass the water. In the degassing system shown in U.S. Pat. No. 3,528,550, the degassing chamber pressure may vary with dialysis solution flow rate, which, in turn, may vary with dialysis conditions, such as patient size, etc. Variations in degassing chamber pressure may affect gas removal. During dialysis it is desirable to control the dialysis solution pressure in the dialyzer. However, changes in the dialysis solution flow rate through the dialyzer cause the dialysis solution pressure to vary.

U.S. Pat. No. 4,348,280 provides a degassing system which functions independently of the dialysis solution flow rates and further provides means for controlling the dialysis solution pressure in the dialyzer as the dialysis solution flow rate changes. In the degassing system proposed by U.S. Pat. No. 4,348,280 water at normal body temperature is fed to a degassing tank that is continuously subjected to a controllable high negative pressure. The pressure is provided by two pumps, one of which draws gas from the tank and another of which draws degassed water from the tank. The degassing tank pressure is thus independent of the dialysis solution flow rate. The dialysis solution pressure and flow rate at the dialyzer are controlled by a pair of flow restrictions which are positioned one upstream and the other downstream of the dialyzer. This permits accurate control of the dialysis solution flow rate and pressure within the dialyzer.

U.S. Pat. No. 4,153,554 discloses an apparatus for delivering a dialysate solution to an artificial kidney. The apparatus prepares the solution by mixing water with a concentrated solution in a predefined ratio. The water enters a heater and then flows into a float tank which is filled with a controlled volume of water by means of a float-controlled valve. Air bubbles are removed from the tank by means of a vacuum pump, which creates a partial vacuum on the float tank and passes air out of a vent. The water is then drawn from the float tank by a supply pump and boosted back to about +5 psig pressure which is maintained by a pressure regulator arranged downstream to the supply pump. A deaerator removes additional air from the water by passing the water over a vertical baffle near an upper air space which is in communication with the top of the float tank by means of a line having a restriction which is adapted to maintain the 5 psig pressure in the deaerator and thus in the water as it leaves the deaerator. Since the supply pump has a constant pressure of about 5 psig to work against, it is possible to maintain a steady flow of dialysate out to an artificial kidney.

The hemodialysis apparatus of U.S. Pat. No. 4,828,693 comprises means for removing air entrapped in the incoming water from the water stream prior to a proportioning pump. The air is removed in a deaeration loop utilizing a deaerator having a float valve and air outlet. The incoming water is fed to a deaerator pressure regulator having an outlet to the deaerator. The deaerator outlet is connected to a pump, thence back to the pressure regulator completing the deaeration loop. The pump creates a negative pressure in the deaerator pressure regulator, drawing the incoming water into the deaerator at which point the entrapped air in the water escapes via the float valve and air outlet at a lower negative pressure. The deaeration pressure regulator controls the negative pressure to a selected value, for example −23 inches of mercury. The incoming water to the deaeration pressure regulator is generally controlled by a first pressure regulator to 12 psig. The outlet water from the deaeration pressure regulator is supplied to the proportioning pump. U.S. Pat. No. 4,828,693 adds a second regulator, termed a back pressure regulator, to receive water from the deaeration pump and to control the pressure of that water to a value higher than 12 psig; for example, 15 psig. The output from the backpressure regulator then supplies the water to the dialysate-proportioning pump. Thus, the pressure of the water to the proportioning pump is independent of the incoming water pressure since the deaerator loop serves as a constant volume source of water to the pump and the pump is independent of the incoming water pressure and flow.

U.S. Pat. No. 4,229,299 describes a dialysate proportioning system provided with deaeration means for removing soluble gases from the heated water prior to passage thereof to the proportioning means. Water containing desolubilized gases is passed from a heater to a first vented tank. Partially deaerated water is removed from the first tank through a conduit into a second vented tank. The conduit has an adjustable flow restrictor which depressurizes the liquid so as to release additional soluble gases therefrom. A pressure sensor is arranged downstream from the restrictor to permit any necessary adjustment of flow restrictor in order to maintain a predetermined pressure level. A vacuum pump is arranged on the conduit downstream from the pressure sensor. In order to enhance removal of soluble gases, a recirculation conduit joins the first tank with the second tank for recirculation of a portion of the finally deaerated water from the second tank to the first tank.

U.S. Pat. No. 5,762,782 describes a water treatment process for use in a dialysate preparation machine wherein warm water is passed through a water pressure regulator past a manually operated valve. The pressure regulator supplies water to the dialysate preparation unit at a substantially constant pressure. The water then passes through a chamber loaded with a carbon filtration agent which removes organic material and dissolved gases from the water.

WO 00/57935 describes an apparatus for the preparation of peritoneal dialysis fluid wherein preheated water passes through a series of components which remove dissolved gas from the water. These components are a proportioning valve, a degassing restrictor, an expansion chamber, a degassing pump and a degassing chamber. In operation, water from the degassing chamber is recirculated via the proportioning valve through the degassing restrictor by the degassing pump. The pressure drop in the water due to the degassing restrictor causes dissolved gas in the water to be forced out of solution and begin to form bubbles in the water. The pressure drop due to the degassing restrictor is a function of the flow rate therethrough, which is maintained constant by recirculation from the degassing chamber, at a flow rate set by the degassing pump.

The prior art includes also AK 100/200/95® dialysis machines (produced by Gambro®) each of which comprises a blood treatment apparatus as in the preamble of claim 1.

SUMMARY OF THE INVENTION

A main aim of the present invention is to effectively remove gas bubbles, especially air bubbles, from the entire circulatory system of a blood treatment apparatus thereby to increase the efficiency of the treatment (e.g. dialyzing) operation.

An advantage of the invention is to provide an economical and efficient degassing system for use in a blood treatment apparatus.

A further advantage of the invention is to provide a pump-type degassing system for use in a blood treatment apparatus in which degasification is effectively and efficiently achieved also when the performances of the degassing pump are reduced.

A further advantage is to enable a desired concentration of gas (neither too high nor too low) in the treatment liquid to be accurately and reliably regulated.

A further advantage is to provide a device for preparation of a treatment liquid provided with a pressure reducer arranged at the inlet of the hydraulic circuit in which there is no need to calibrate the pressure reducer when the device is installed at different altitudes.

Another advantage of the invention is that it provides a device for removing gases, which will enable a high separation rate to be attained with a compact and simple type of construction.

A further advantage of this invention is that it provides a pump-type degassing system for use in a blood treatment apparatus which is flexible in that it is adaptable for use under varying conditions and in which the relationship between degassing and other conditions (altitude, dialysis liquid flow rate, dialyzing liquid pressure, pump performances, etc.) will not undesirably change during operation.

A further advantage of the invention consists in the fact that the efficiency of the degassing pump can be maximized by appropriately selecting the degassing pressure set point.

These aims and advantages and more besides, which will better emerge from the description that follows, are attained by a blood treatment apparatus according to one or more of the accompanying claims.

Further characteristics and advantages of the present invention will better emerge from the detailed description that follows, of at least a preferred embodiment of the invention, illustrated by way of non-limiting example in the accompanying figures of the drawings.

BRIEF DESCRIPTION OF THE DRAWINGS

The description will follow herein below, with reference to the figures of the drawings, provided as a non-limiting example and in which.

DETAILED DESCRIPTION

Figure 1:
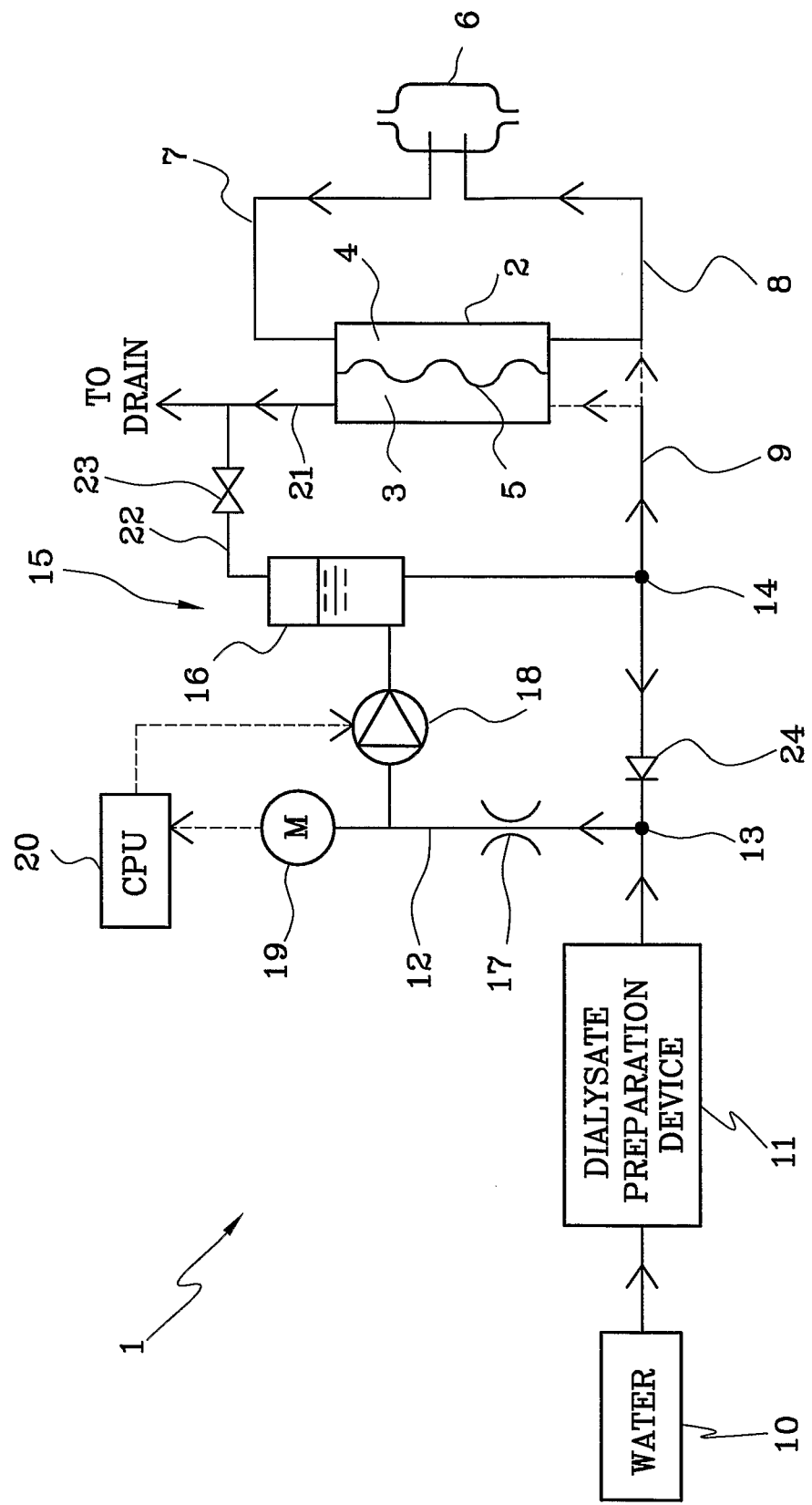
FIG. 1 is a schematic diagram of a blood treatment apparatus according to a first embodiment of the present invention.

With reference to the above-cited FIG. 1 of the drawings, 1 denotes in its entirety a blood treatment apparatus, particularly a hemodialysis or hemo(dia)filtration apparatus.

The blood treatment apparatus 1 comprises a blood treatment unit (hemodialyser or hemo(dia)filter) 2 having a fluid chamber 3, a blood chamber 4, and a semipermeable membrane 5 separating the fluid chamber 3 from the blood chamber 4.

An extracorporeal blood circuit connects a patient vascular access 6 with the blood chamber 4. The extracorporeal blood circuit comprises an arterial line 7 for transporting the blood to be treated from the vascular access 6 to an inlet of the blood compartment 4, and a venous line 8 for returning the treated blood to the vascular access 6. The extracorporeal blood circuit can be any extracorporeal blood circuit used during a blood treatment in the prior art.

The blood treatment apparatus 1 comprises a treatment fluid supply line 9 comprising a water inlet connected to a water source 10, and a treatment fluid outlet connected to the fluid chamber 3 (hemodialysis treatment) and/or to the extracorporeal blood circuit (hemodiafiltration/hemofiltration treatment), in particular to the arterial line 7 and/or to the venous line 8 (pre- and/or post-dilution).

The blood treatment apparatus 1 comprises a preparation device 11 connected to the treatment fluid supply line 9 to prepare the treatment fluid from water and concentrates. In this specific case the treatment fluid is a dialysis fluid (dialysate) which can be used to form a substitution fluid for hemo (dia)filtration treatments.

The blood treatment apparatus 1 further comprises a degassing line 12 having an inlet 13 for receiving gas-containing fluid coming from the water inlet, and an outlet 14 for supplying degassed fluid to the treatment fluid outlet. In the present embodiment the treatment fluid supply line 9 has a first junction point, which in this specific case coincides with the inlet 13 of the degassing line 12 and from which the degassing line 12 branches off, and a second junction point, which in this specific case coincides with the outlet 14 of the degassing line 12 and into which the degassing line 12 flows into. In the present embodiment the preparation device 11 is located between the water inlet and the gas-containing fluid inlet 13; in another embodiment (not illustrated) the preparation device 11 is located between the degassed fluid outlet 14 and the treatment fluid outlet.

A degassing unit 15 is operatively connected to the degassing line 12. the degassing unit 15 comprises a gas separator 16 for separating the gas in the gas-containing fluid flowing in the degassing line 12, a flow restrictor 17 for reducing the pressure of the fluid flowing in the degassing line 12, a degassing pump 18 for circulating the fluid in the degassing line 12, a pressure sensor 19 for emitting a pressure signal indicative of the pressure in the degassing line 12, and a control unit 20 designed to control the speed of the degassing pump 18 on the basis of the pressure signal emitted by the pressure sensor 19.

In the present embodiment the gas separator 16 comprises a gas separation chamber. The signal used by the control unit 20 to control the degassing pump 18 is one that indicates the absolute pressure in the degassing line 12. In the present embodiment the pressure sensor 19 is an absolute pressure sensor designed to emit an absolute pressure signal. The degassing pump 18 has a delivering outlet connected to a fluid inlet of the gas separator 16. The degassing pump 18 is located in the degassing line 12 between the restrictor 17 and the gas separator 16. The degassing pump 18 is located in the degassing line 12 between the pressure sensor 19 and the gas separator 16. The pressure sensor 19 is located in the degassing line 12 between the restrictor 17 and the gas separator 16. The pressure sensor 19 is located in the degassing line 12 between the restrictor 17 and the degassing pump 18. In this specific case the degassing pump 18 is a positive displacement pump (e.g. a gear pump).

The blood treatment apparatus 1 further comprises a discharge line 21 connecting the fluid chamber 3 with a drain. The gas separator 16 comprises a gas outlet connected through a vent line 22 to the discharge line 21. The vent line 22 is provided with a closing valve 23 controlled by the control unit 20.

A one-way valve 24 is arranged in the treatment fluid supply line 9 between the first junction point (inlet 13) and the second junction point (outlet 14) so as to block the flow from the inlet 13 to the outlet 14.

During operation the dialysate flow rate in the degassing line 12 should be higher than (e.g. twice as high as) the flow rate in the treatment fluid supply line 9. The fluid (in this case dialysate) which enters the inlet 13 contains air bubbles and dissolved air. To reduce air in the fluid, the fluid is forced to pass through the deaeration restrictor 17. The speed of the pump 18 is controlled from the pressure, in particular the absolute pressure, in the degassing line 12. In this specific case the pump speed is controlled in a closed loop on the basis of the pressure signal emitted by the pressure sensor 19. In particular the degassing pump 18 controls the pressure in the degassing line 12 at a constant absolute pressure (e.g. 100 mmHg) set to achieve a desired degassing effect, particularly a desired percentage of gas in the treatment fluid. In this way the desired amount of gas in the treatment fluid is always achieved under varying conditions (decrease in efficiency of the degassing pump 18, narrowing of the restrictor 17, difference in altitude, etc.).

The removed air is collected in the gas separator (chamber) 16 and periodically vented to the drain. In this case the liquid level in the separation chamber is monitored by a level sensor (not shown). When the level sensor detects air in the chamber, the valve 23 is opened to vent the accumulated air. The valve 23 is closed when the level sensor detects liquid again.

Figure 2:
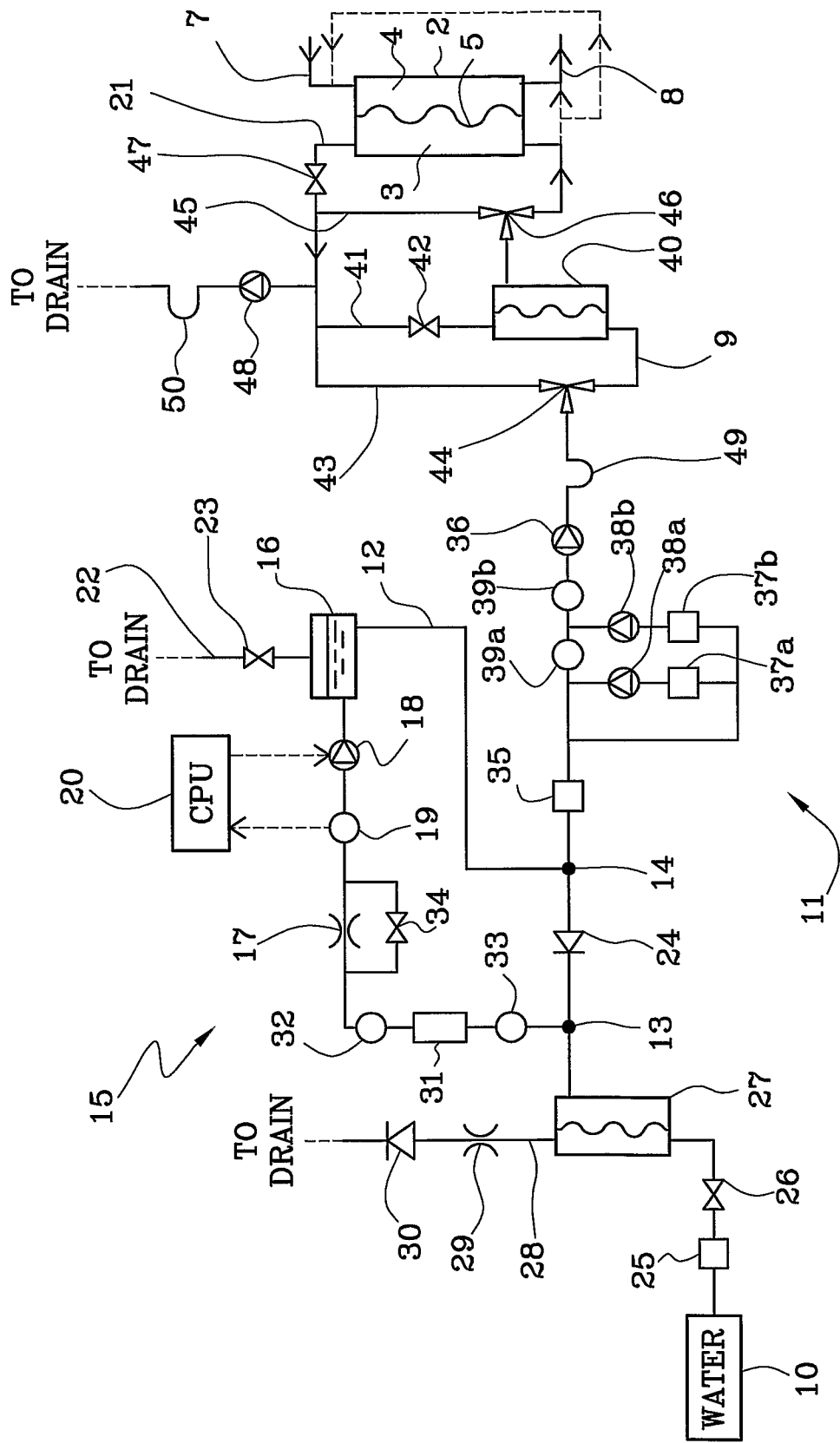
FIG. 2 is a schematic diagram of a blood treatment apparatus according to a second embodiment of the present invention.

We will refer now to FIG. 2 which shows a second embodiment according to the invention. The numbering of FIG. 1 has been maintained also in FIG. 2 for analogous elements.

The blood treatment apparatus (hemodialysis or hemo(dia)filtration apparatus) of FIG. 2 comprises a blood treatment unit (hemodialyser or hemo(dia)filter) 2 having a fluid chamber 3, a blood chamber 4, and a semipermeable membrane 5 separating the fluid chamber 3 from the blood chamber 4.

An extracorporeal blood circuit connects a patient vascular access (not shown) with the blood chamber 4. The extracorporeal blood circuit comprises an arterial line 7 and a venous line 8.

The blood treatment apparatus 1 comprises a treatment fluid supply line 9 having a water inlet connected to a water source 10, and a treatment fluid outlet connected to the fluid chamber 3 (hemodialysis treatment) and/or to the arterial line 7 and/or to the venous line 8 (hemodiafiltration/hemofiltration treatment with pre- and/or post-dilution).

The blood treatment apparatus 1 comprises a preparation device 11 connected to the treatment fluid supply line 9 to prepare the treatment fluid from water and concentrates. In this specific case the treatment fluid is a dialysis fluid (dialysate) which can be used to form a substitution fluid for hemo(dia)filtration treatments. The treatment fluid preparation device 11 can comprise a central delivery system connected to the blood treatment apparatus 1, or a device for preparing a fluid from water and concentrates.

The blood treatment apparatus 1 further comprises a degassing line 12 having an inlet 13 to receive gas-containing fluid coming from the water inlet, and an outlet 14 for supplying degassed fluid to the treatment fluid outlet. In this specific case the treatment fluid supply line 12 has a first junction point, which in this specific case coincides with the inlet 13 of the degassing line 12 and from which the degassing line 12 branches off, and a second junction point, which in this specific case coincides with the outlet 14 of the degassing line 12 and into which the degassing line 12 flows. In this specific case the preparation device 11 is located between the degassed fluid outlet 14 and the treatment fluid outlet.

A degassing unit 15 is operatively connected to the degassing line 12. The degassing unit 15 comprises a gas separator 16 for separating the gas in the gas-containing fluid flowing in the degassing line 12, a flow restrictor 17 for reducing the pressure of the fluid flowing in the degassing line 12, a degassing pump 18 for circulating the fluid in the degassing line 12, a pressure sensor 19 for emitting a pressure signal indicative of the pressure in the degassing line 12, and a control unit 20 designed to control the speed of the degassing pump 18 on the basis of the pressure signal emitted by the pressure sensor 19.

In the present embodiment the gas separator 16 comprises a gas separation chamber. The signal used by the control unit 20 to control the degassing pump 18 is a signal indicative of the absolute pressure in the degassing line 12. In this specific case the pressure sensor 19 is an absolute pressure sensor designed to emit an absolute pressure signal. The degassing pump 18 has a delivering outlet connected to a fluid inlet of the gas separator 16. The degassing pump 18 is located in the degassing line 12 between the restrictor 17 and the gas separator 16. The degassing pump 18 is located in the degassing line 12 between the pressure sensor 19 and the gas separator 16. The pressure sensor 19 is located in the degassing line 12 between the restrictor 17 and the gas separator 16. The pressure sensor 19 is located in the degassing line 12 between the restrictor 17 and the degassing pump 18. In the present embodiment the degassing pump 18 is a positive displacement pump (e.g. a gear pump).

The blood treatment apparatus 1 further comprises a discharge line 21 connecting the fluid chamber 3 with a drain. The gas separator 16 comprises a gas outlet connected through a vent line 22 to the drain. The vent line 22 can be connected to the discharge line 21. The vent line 22 is provided with a closing valve 23 controlled by the control unit 20.

A one-way valve 24 is arranged in the treatment fluid supply line 9 between the first junction point (inlet 13) and the second junction point (outlet 14) so as to block the flow from the inlet 13 to the outlet 14.

The apparatus of FIG. 2 further comprises a pressure reducer 25 arranged immediately after the water inlet to control the pressure by restricting the fluid passage. A normally closed inlet valve 26 is located downstream the pressure reducer 25. The apparatus of FIG. 2 comprises a first ultrafilter 27 designed to retain bacteria or endotoxin. The first ultrafilter has a first chamber (retentate chamber) separated from a second chamber (permeate chamber) by a semipermeable membrane. A flushing line 28 connects an outlet of the first chamber of the first ultrafilter with the drain. An orifice 29 is arranged in the flushing line 28 to limit the flow rate of fluid flushed through the first chamber and the flushing line 28 and then into the drain. A check valve 30 prevents a back-flow coming from the drain polluting the first ultrafilter 27.

A heater 31 is arranged in the degassing line 12 upstream the restrictor 17 to heat the incoming fluid. A temperature sensor 32 measures the temperature of the fluid in the degassing line 12 (downstream of the heater 31). The control unit 20 controls the heater 31 to ensure that the temperature measured by the sensor 32 is within a desired range. A flow switch 33 is arranged in the degassing line 12. The control unit 20 recognizes an alarm situation (and disconnects the power from the heater 31, for example) when the flow rate through the flow switch 33 is lower than a predetermined value. In another embodiment (not shown) the heater 31 is located downstream of the restrictor 17, e.g. between the restrictor 17 and the degassing pump 18, or between the restrictor 17 and the pressure sensor 19.

A restrictor bypass valve 34 is arranged in a bypass line connected to the degassing line 12, for bypassing the restrictor 17. The restrictor bypass valve 34, which is normally closed, is opened during a heat disinfection procedure—which serves to disinfect the hydraulic circuit of the blood treatment apparatus—and is closed during a blood treatment procedure. When the restrictor bypass valve 34 is opened during a heat disinfection procedure, the degassing restrictor 17 is bypassed in order to prevent the heated liquid (water) from boiling.

A pressure regulator 35 is arranged in the treatment fluid supply line 9 between the degassing line 12 and a supply pump 36 circulating a fluid in the treatment fluid supply line 9. The pressure regulator 35 is arranged downstream of the degassing line 12. The pressure regulator 35 is set to maintain a desired pressure in the concentrate sources 37a and 37b. When the concentrate sources comprise cartridges of dry concentrates a moderate overpressure inside the cartridges can be desirable. The pressure regulator 35 avoids a too-low pressure causing the formation of gas bubbles upstream of the supply pump 36. Moreover the pressure regulator 35 prevents or reduces pressure spikes coming from the gas separator 16 (gas separation chamber or bubble trap) during the above-described gas evacuation.

The treatment fluid (dialysate) preparation device 11 comprises at least two injection lines each operatively associated to a concentrate source 37a and 37b (liquid or solid concentrates), to a dosing pump 38a and 38b, and to a conductivity sensor 39a and 39b controlling a respective dosing pump to a set conductivity value. The injection lines are supplied with a solvent (e.g. water) from a line branching off from the treatment fluid supply line 9.

The apparatus of FIG. 2 comprises a second ultrafilter 40 designed to retain bacteria or endotoxin. The second ultrafilter 40 has a first chamber (retentate chamber) separated from a second chamber (permeate chamber) by a semipermeable membrane. A flushing line 41 connects an outlet of the first chamber of the second ultrafilter 40 with the discharge line 21. The flushing line 41 is provided with a flushing valve 42 which is periodically (or under predetermined conditions) opened to tangentially flush the second ultrafilter 40.

A first bypass line 43 is arranged upstream of the second ultrafilter 40 to connect the supply line 9 with the discharge line 21. The first bypass line 43 is provided with a first bypass valve 44. A second bypass line 45 is arranged downstream of the second ultrafilter 40 to connect the supply line 9 with the discharge line 21. The second bypass line 45 is provided with a second bypass valve 46. A closing valve 47 is arranged in the discharge line 21 before the second bypass line 45. A discharge pump 48 is arranged downstream of the flushing line 41. The discharge pump 48 is arranged downstream of the first and second bypass lines 43 and 45. The discharge pump 48 circulates the fluid towards the drain. A fluid balance system controls the discharge pump 48 (and the supply pump 36) to regulate the weight loss of a patient undergoing a blood treatment. In this specific case the fluid balance system comprises an upstream flowmeter 49 arranged before the blood treatment unit 2 in the supply line 9, and a downstream flowmeter 50 arranged after the blood treatment unit 2 in the discharge line 21.

The control unit 20 is designed to control the degassing pump 18 (during the treatment) at a flow rate which is greater than that of the treatment fluid supply pump 36. During the treatment the valve 34 is closed and the fluid (water) is passed through the degassing restrictor 17. The degassing system of the FIG. 2 apparatus operates as above described in order to reduce gas in the fluid.

The control unit 20 is designed to control the degassing pump 18 at a predetermined degassing pressure set point.

The degassing pressure can be set as low as possible in order to maximize the degassing performance, i.e. the removal of oxygen. However, there are some limitations as to how low the degassing pressure can be set. For example, a too-low degassing pressure may result in cavitation in the pump causing increased wear and/or a loss of pump efficiency.

The selection of the degassing set point may be a trade-off between degassing performance and other requirements such as, e.g., pump life, cost and power consumption.

In a further embodiment (not shown) a blood treatment apparatus differs from the apparatus of FIG. 1 (or FIG. 2) only in that the pressure signal that indicates the absolute pressure in the degassing line 12 may be supplied by processing two pressure signals emitted by a first relative pressure sensor arranged in the degassing line 12 (at the same location of the absolute pressure sensor 19) and a second pressure sensor indicating the atmospheric pressure. A calculation unit may calculate an absolute pressure value from said two pressure signals, e.g. as a difference between the pressure values indicated by the two pressure signals. The control unit 20 may include the calculation unit.

In a further embodiment (not shown) a blood treatment apparatus differs from the apparatus of FIG. 1 (or FIG. 2) only in that the degassing line forms a tract (initial, intermediate, or final tract) of the treatment fluid supply line without forming a loop between two junction points thereof. In this embodiment the degassing line and the treatment fluid supply line form a continuous fluid line, whereby the flow rate of the degassing line is equal to the flow rate of the treatment fluid supply line and the supply pump of the treatment fluid supply line may act as degassing pump of the degassing line.

LEGEND

1 Blood treatment apparatus
2 Blood treatment unit
3 Fluid chamber
4 Blood chamber
5 Semipermeable membrane
6 Patient vascular access
7 Arterial line
8 Venous line
9 Treatment fluid supply line
10 Water source
11 Treatment fluid preparation device
12 Degassing line
13 Inlet of degassing line 14 Outlet of degassing line
15 Degassing unit
16 Gas separator
17 Flow restrictor
18 Degassing pump
19 Pressure sensor
20 Control unit
21 Discharge line
22 Vent line
23 Closing valve
24 One-way valve
25 Pressure reductor
26 Inlet valve
27 First ultrafilter
28 Flushing line
29 Orifice
30 Check valve
31 Heater
32 Temperature sensor
33 Flow switch
34 Restrictor bypass valve
35 Pressure regulator
36 Supply pump
37 Concentrate sources (37a, 37b)
38 Dosing pumps (38a, 38b)
39 Conductivity sensors (39a, 39b)
40 Second ultrafilter
41 Flushing line
42 Flushing valve
43 First bypass line
44 First bypass valve
45 Second bypass line
46 Second bypass valve
47 Closing valve
48 Discharge pump
49 Upstream flowmeter
50 Downstream flowmeter

The invention claimed is:

1. A blood treatment apparatus comprising:
a blood treatment unit having a fluid chamber, a blood chamber, and a semipermeable membrane separating the fluid chamber from the blood chamber;
an extracorporeal blood circuit connecting a patient vascular access with said blood chamber;
a treatment fluid supply line comprising a gas-containing fluid inlet connected to a gas-containing fluid source, and a treatment fluid outlet connected to said fluid chamber and/or to said extracorporeal blood circuit;
a degassing line having a degassing line inlet for receiving gas-containing fluid coming from said gas-containing fluid inlet, and a degassing line outlet for supplying degassed fluid to said treatment fluid outlet;
a degassing unit operatively connected to said degassing line, said degassing unit comprising:
  a degassing pump for flowing the fluid in said degassing line from said degassing line inlet to said degassing line outlet,
  a gas separator for separating the gas in the gas-containing fluid flowing in said degassing line, and
  a flow restrictor for reducing the pressure of the fluid flowing in said degassing line, wherein said apparatus further comprises:
an absolute pressure sensor means configured to emit an absolute pressure signal indicative of an absolute pressure in said degassing line, and
a control unit programmed to control the speed of said degassing pump from said absolute pressure signal.

2. The apparatus of claim 1, wherein said absolute pressure sensor means comprises an absolute pressure sensor.

3. The apparatus of claim 1, comprising a discharge line connecting the fluid chamber with a drain.

4. The apparatus of claim 3, wherein the gas separator comprises a gas outlet connected through a vent line to the discharge line.

5. The apparatus of claim 1, wherein the degassing pump has a delivering outlet connected to a fluid inlet of the gas separator.

6. The apparatus of claim 1, comprising a heater located in the degassing line for heating the fluid flowing in the degassing line.

7. The apparatus of claim 6, wherein said flow restrictor is located in the degassing line between the heater and the gas separator or the degassing pump.

8. The apparatus of claim 6, wherein said heater is located in the degassing line between said flow restrictor and said degassing pump or said absolute pressure sensor means.

9. The apparatus of claim 6, wherein said heater is located in the degassing line downstream of said flow restrictor.

10. The apparatus of claim 6, wherein said heater is located in the degassing line downstream of said absolute pressure sensor means.

11. The apparatus of claim 1, wherein the degassing pump is located in the degassing line between the flow restrictor and the gas separator.

12. The apparatus of claim 1, wherein the degassing pump is located in the degassing line between the absolute pressure sensor means and the gas separator.

13. The apparatus of claim 1, wherein the absolute pressure sensor means are located in the degassing line between the flow restrictor and the gas separator.

14. The apparatus of claim 1, wherein the absolute pressure sensor means are located in the degassing line between the flow restrictor and the degassing pump.

15. The apparatus of claim 1, wherein the absolute pressure sensor means are located in the degassing line downstream of the flow restrictor.

16. The apparatus of claim 1, further comprising a treatment fluid preparation device connected to said treatment fluid supply line to prepare the treatment fluid from water and concentrates.

17. The apparatus of claim 16, wherein the treatment fluid preparation device is located between said degassing line outlet and said treatment fluid outlet.

18. The apparatus of claim 1, wherein the treatment fluid supply line has a first junction point and a second junction point, the degassing line forming a loop between the first junction point and the second junction point.

19. The apparatus of claim 18, wherein a one-way valve is arranged in the treatment fluid supply line between said first junction point and said second junction point.

20. The apparatus of claim 1, comprising a treatment fluid supply pump for displacing fluid through the treatment supply line.

21. The apparatus of claim 20, wherein said treatment fluid supply pump is arranged in said treatment supply line.

22. The apparatus of claim 20, wherein said control unit is programmed to control said treatment fluid supply pump to flow fluid through the treatment supply line at a first flow rate and to control said degassing pump to flow fluid through the degassing line at a second flow rate, said first flow rate being lower than said second flow rate.

23. The apparatus of claim 1, wherein said gas separator comprises a gas separation chamber.

24. The apparatus of claim 1, wherein said absolute pressure sensor means comprises a first pressure sensor for emitting a first pressure signal indicative of a relative pressure in said degassing line, a second pressure sensor for emitting a second pressure signal indicative of the atmospheric pressure, and a calculation unit programmed to calculate an absolute pressure value from said first and second pressure signals.

25. A blood treatment apparatus comprising:
- a blood treatment unit having a fluid chamber, a blood chamber, and a semipermeable membrane separating the fluid chamber from the blood chamber;
- an extracorporeal blood circuit connecting a patient vascular access with said blood chamber;
- a treatment fluid supply line comprising a gas-containing fluid inlet connected to a gas-containing fluid source, and a treatment fluid outlet connected to said fluid chamber and/or to said extracorporeal blood circuit;
- a degassing line having a degassing line inlet for receiving gas-containing fluid coming from said gas-containing fluid inlet, and a degassing line outlet for supplying degassed fluid to said treatment fluid outlet;
- a degassing unit operatively connected to said degassing line, said degassing unit comprising:
  - a degassing pump for flowing the fluid in said degassing line from said degassing line inlet to said degassing line outlet,
  - a gas separator for separating the gas in the gas-containing fluid flowing in said degassing line, and
  - a flow restrictor for reducing the pressure of the fluid flowing in said degassing line, wherein said apparatus further comprises:
- an absolute pressure sensor means configured to emit an absolute pressure signal indicative of an absolute pressure in said degassing line, and
- a control unit programmed to control the speed of said degassing pump from said absolute pressure signal, wherein
- the treatment fluid supply line has a first junction point and a second junction point, the degassing line forming a loop between the first junction point and the second junction point.

26. A blood treatment apparatus comprising:
- a blood treatment unit having a fluid chamber, a blood chamber, and a semipermeable membrane separating the fluid chamber from the blood chamber;
- an extracorporeal blood circuit connecting a patient vascular access with said blood chamber;
- a treatment fluid supply line comprising a gas-containing fluid inlet connected to a gas-containing fluid source, and a treatment fluid outlet connected to said fluid chamber and/or to said extracorporeal blood circuit;
- a degassing line having a degassing line inlet for receiving gas-containing fluid coming from said gas-containing fluid inlet, and a degassing line outlet for supplying degassed fluid to said treatment fluid outlet;
- a degassing unit operatively connected to said degassing line, said degassing unit comprising:
  - a degassing pump for flowing the fluid in said degassing line from said degassing line inlet to said degassing line outlet, wherein the degassing pump is located in the degassing line between the flow restrictor and the gas separator,
  - a gas separator for separating the gas in the gas-containing fluid flowing in said degassing line, and
  - a flow restrictor for reducing the pressure of the fluid flowing in said degassing line, wherein said apparatus further comprises:
- an absolute pressure sensor means configured to emit an absolute pressure signal indicative of an absolute pressure in said degassing line, and
- a control unit programmed to control the speed of said degassing pump from said absolute pressure signal, wherein the control unit is programmed to control the speed of said degassing pump so that the pressure in the degassing line is set at a constant pressure to achieve a desired percentage of gas in the fluid flowing in said degassing line.

* * * * *

UNITED STATES PATENT AND TRADEMARK OFFICE
CERTIFICATE OF CORRECTION

PATENT NO.      : 8,449,487 B2
APPLICATION NO. : 12/516786
DATED           : May 28, 2013
INVENTOR(S)     : Hovland et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 989 days.

Signed and Sealed this
Eighth Day of September, 2015

Michelle K. Lee
*Director of the United States Patent and Trademark Office*